US010514358B2

(12) United States Patent
Matysik et al.

(10) Patent No.: US 10,514,358 B2
(45) Date of Patent: Dec. 24, 2019

(54) METHOD AND DEVICE FOR TWO-DIMENSIONAL SEPARATION OF IONIC SPECIES

(71) Applicant: UNIVERSITÄT REGENSBURG, Regensburg (DE)

(72) Inventors: Frank-Michael Matysik, Regensburg (DE); Andrea Beutner, Etzenricht (DE); Jonas Mark, Kohlberg (DE); Sven Kochmann, Regensburg (DE)

(73) Assignee: UNIVERSITÄT REGENSBURG, Regensburg (DE)

( * ) Notice: Subject to any disclaimer, the term of this patent is extended or adjusted under 35 U.S.C. 154(b) by 126 days.

(21) Appl. No.: 15/302,780

(22) PCT Filed: Apr. 23, 2015

(86) PCT No.: PCT/EP2015/058837
§ 371 (c)(1),
(2) Date: Oct. 7, 2016

(87) PCT Pub. No.: WO2015/162219
PCT Pub. Date: Oct. 29, 2015

(65) Prior Publication Data
US 2017/0030860 A1 Feb. 2, 2017

(30) Foreign Application Priority Data

Apr. 25, 2014 (EP) .................................... 14166119
Feb. 26, 2015 (EP) .................................... 15156828

(51) Int. Cl.
*G01N 27/453* (2006.01)
*G01N 27/447* (2006.01)
(Continued)

(52) U.S. Cl.
CPC ..... *G01N 27/44743* (2013.01); *B01D 15/361* (2013.01); *G01N 27/44791* (2013.01);
(Continued)

(58) Field of Classification Search
CPC ............. G01N 2030/965; G01N 30/02; G01N 27/44791; G01N 27/453; G01N 27/44743
See application file for complete search history.

(56) References Cited

U.S. PATENT DOCUMENTS

| 4,999,098 A | 3/1991 | Pohl et al. |
| 5,131,998 A | 7/1992 | Jorgenson et al. |

(Continued)

FOREIGN PATENT DOCUMENTS

| DE | 19717738 C1 | 8/1998 |
| WO | WO-94/020840 A1 | 9/1994 |

(Continued)

OTHER PUBLICATIONS

Kar et al., "Direct Coupling of Ion Chromatography with Suppressed Conductometric Capillary Electrophoresis," Journal of Microcolumn Separations, vol. 8, issue 8, pp. 561-568 (Year: 1996).*

(Continued)

*Primary Examiner* — Alexander S Noguerola
(74) *Attorney, Agent, or Firm* — Ballard Spahr LLP

(57) ABSTRACT

The invention relates to a method which realizes a two-dimensional separation of ionic species on the basis of the online coupling of ion chromatography (IC) and capillary electrophoresis (CE). A device for IC×CE coupling, its implementation in terms of two alternatives, the connection to a mass spectrometric detector, and corresponding application are described.

12 Claims, 4 Drawing Sheets

(51) Int. Cl.
  *G01N 30/16* (2006.01)
  *G01N 30/96* (2006.01)
  *B01D 15/36* (2006.01)
  *G01N 30/20* (2006.01)

(52) U.S. Cl.
  CPC ............ *G01N 30/16* (2013.01); *G01N 30/20* (2013.01); *G01N 30/96* (2013.01); *G01N 27/44782* (2013.01); *G01N 2030/204* (2013.01); *G01N 2030/965* (2013.01)

(56) References Cited

U.S. PATENT DOCUMENTS

| | | | | |
|---|---|---|---|---|
| 5,646,048 | A | * | 7/1997 | Templin ........... G01N 27/44743 204/601 |
| 5,958,215 | A | * | 9/1999 | Kuhr .................. G01N 27/3277 204/400 |
| 2004/0168915 | A1 | | 9/2004 | He et al. |

FOREIGN PATENT DOCUMENTS

| | | |
|---|---|---|
| WO | WO-03/087773 A2 | 10/2003 |
| WO | WO-2011/091030 A1 | 7/2011 |

OTHER PUBLICATIONS

Product specificaiotns brochure entitled "Thermo Scientific Reagent-Free Ion Chromatography Systems with Eluent Generation for IC without Manually Prepared Eluents," ThermoScientific, 2014 (Year: 2014).*

Pavel Jandera, Comprehensive two-dimensional liquid chromatography—practical impacts of theoretical considerations. Central European Journal of Chemistry Jun. 2012 vol. 10, Issue 3, pp. 844-875.

Brudin et al., Comprehensive two-dimensional liquid chromatography: Ion chromatography x reversed-phase liquid chromatography for separation of low-molar-mass organic acids, journal of Chromatography A, 1217 (2010) pp. 6742-6746.

Mellors et al.,Hybrid Capillary/Microfluidic System for Comprehensive Online Liquid Chromatography-Capillary Electrophoresis-Eiectrospray Ionization-Mass Spectrometry, Analytical Chemistry. (2013) 85, 4100-4106.

Niegel et al., Fast separations by capillary electrophoresis hyphenated to electrospray ionization time-of-flight mass spectrometry as a tool for arsenic speciation analysis, Analyst, (2012) 137, 1956-1962.

Frank-Michael Matysik, Capillary batch injection—A new approach for sample introduction into short-length capillary electrophoresis with electrochemical detection, Electrochemistry Communications 8 (2006) pp. 1011-1015.

International Search Report dated Jun. 26, 2015 for International Application No. PCT/EP2015/058837, which was filed on Apr. 23, 2015 and published as WO 2015/162219 on Oct. 29, 2015 (Inventor-Frank-Michael Matysik) (4 pages).

Written Opinion dated Jun. 26, 2015 for International Application No. PCT/EP2015/058837, which was filed on Apr. 23, 2015 and published as WO 2015/162219 on Oct. 29, 2015 (Inventor-Frank-Michael Matysik) (7 pages).

* cited by examiner

METHOD AND DEVICE FOR TWO-DIMENSIONAL SEPARATION OF IONIC SPECIES

CROSS-REFERENCE TO RELATED APPLICATIONS

This application is a U.S. National Phase Application of International Application No. PCT/EP2015/058837, filed Apr. 23, 2015, which claims priority to European Patent Application No. 14166119.9, filed Apr. 25, 2014, and European Patent Application No. 15156828.4, filed Feb. 26, 2015, each of which are hereby incorporated by reference in their entirety.

FIELD OF THE INVENTION

The invention is concerned with a method and a device for two-dimensional separation of ionic species using ion chromatography (IC) and capillary electrophoresis (CE).

BACKGROUND

In the last decades a plurality of analytical methods using chromatographic technology has been provided. Further refined methods have been developed by coupling two chromatographic techniques. An example is comprehensive two-dimensional gas chromatography (GC×GC), in which usually a long nonpolar GC column is coupled with a short polar GC column, with the aim to improve the so-called peak capacity, which is a performance measure describing the number of resolved signals of the analytical separation in a specified time slot. The separation on the long column leads to typical retention times in the minute range, while fast separations with orthogonal selectivity can be realized in the second range on the short column. The results of the GC×GC technique can be presented as so-called contour plots, wherein signal intensities are assigned to the retention times of the first and second separation dimension on the basis of a color scale.

In analogy to the GC×GC, other two-dimensional chromatography systems have been described for separations with liquid mobile phases. Two-dimensional liquid chromatography (LC×LC) has found increased use [1]. Recently, a combination of liquid chromatography (LC) and chip electrophoresis has been described [2]. Also known are two-dimensional separations of various electrophoretic separation methods as well as the coupling of ion chromatography (IC) and reversed phase liquid chromatography [3].

For the separation of ionic species ion chromatography (IC) and capillary electrophoresis (CE) are the major instrumental techniques. Both separation methods are based on completely different separation mechanisms.

Ion chromatography is a method that allows the separation of ions and protonated/deprotonated polar molecules based on their affinity to an ion exchanger.

Capillary electrophoresis is an analytical technique that separates ions based on their electrophoretic mobility with the use of an applied voltage. The electrophoretic mobility is dependent upon the charge and the hydrodynamic radius of an ionic species. It has been shown that CE separations can be carried out in short fused silica capillaries in conjunction with mass spectrometry in the migration time range of a few seconds [4].

Although two-dimensional systems were known, a combination of ion exchange chromatography methods and electrophoresis based methods was not contemplated in the past for various reasons. In particular, the relatively slow separation speed of conventional CE based on the use of long capillaries was deemed to exclude the construction of a corresponding two-dimensional separation system. A difference between both systems is the fundamentally different flow characteristic that develops in the injection cell around the CE separation capillary.

One crucial aspect for the technical realization of two-dimensional separations with the conversion of all sample components from the first to the second dimension of separation is the use of a modulator which controls the transfer from the first to the second dimension. In DE 19717738C1 [5] it has been found that with the process of capillary batch injection analysis (CBIA) small sample volumes in the nanoliter range, which are handled by means of a capillary coupled to a microliter syringe, may be injected directly onto the surface of a sensor in a detection cell filled with electrolyte solution, and the small injected sample volumes may then be dispersed in the electrolyte reservoir by a stirrer, such that the measurements can be repeated at a high frequency, showing only a negligible base line drift due to the large dilution in the electrolyte reservoir. It has been shown later that the CBIA concept can also be adapted as an injection concept for CE [6]. However, both in the classical CBIA as well as in the case of CBIA-CE, only discrete sample volumes can be taken up by means of a capillary and then injected to a sensor surface or to the inlet of a CE capillary, respectively.

Batch processing is labor-intensive and time consuming, as for every batch, the system has to be cleaned and the solutions have to be prepared before the system is ready for the next batch. Furthermore, batch processing is more error-prone due to being labor-intensive, and comparison of the results of the analysis of the different batch samples can vary due to the practically separate experimental setup conditions for every batch.

It was an objective of the present invention to provide a device and a method for an improved separation of ionic species, which has increased peak capacity, is more cost-effective, and less error-prone than the methods known and used in conventional manner.

SUMMARY OF THE PRESENT INVENTION

The present invention provides an improved method of separating ionic species and a device for use of such a method.

It was surprisingly found that a highly efficient separation of ionic species is possible by coupling ion chromatography (IC) and capillary electrophoresis (CE) using a modulator as defined in the claims. The IC×CE method of the present invention is a two-dimensional separation system that allows a high orthogonality for ion separation and represents a very attractive new technology in the field of separation processes. It was found that a combination of IC with retention times that are typically in the range of 5-30 minutes, with a CE system is possible when using the specific modulator providing a sequential injection of small volume segments in the nanoliter range into the CE system at time intervals of a few seconds.

The devices and methods of the present invention allow continuous operation, i.e. IC can be coupled to CE on-line, which means that both separation methods can be operated without interruption of the basic setup. This was accomplished by the modulators of the invention used to control the transfer of the IC carrier flow to the CE system. The new system offers many advantages and can be used to separate charged molecules, like mixtures of nucleotides and cyclic nucleotides, in an efficient manner.

The method of the present invention uses IC in the first dimension and CE in the second dimension. Both methods per se are well-known in the field and the known methods and devices can be used in common manner and the optimal conditions can be found based on the species to be analyzed.

The critical part of the method is the transfer of the IC effluent to the CE system which is outlined below in detail.

Thus, a device of the present invention comprises an ion chromatography (IC) system, a capillary electrophoresis (CE) system, and a modulator.

The IC system can be a known system including a suppressor which allows obtaining an effluent with a carrier that is highly pure water. The system is operated continuously with retention times normally being in the range of 5 to 30 minutes, depending on the sample composition. In a preferred embodiment, the IC system is a capillary IC system.

The second system is a CE system that comprises an electrolyte vessel with electrophoresis buffer, and a high voltage electrode. CE systems are known per se, for the present invention a capillary CE system is used with a short capillary.

Both systems are connected via a transfer capillary which provides for the transfer of the IC effluent to the CE system and an injector which provides for the injection of volume segments of the IC effluent into the CE capillary. The effluent is continuously provided and transferred through the transfer capillary and volume segments are injected in time increments, i.e. continuously in the form of discrete increments. The injection of volume segments is an essential part of the method of the present invention. A modulator regulates the injection to avoid that in the immediate area around inlet of the CE capillary a breakdown of the electrophoretic current occurs. This can happen when the incoming IC carrier flow from the outlet of the transfer capillary within the electrolyte vessel filled with electrophoresis buffer is continuously very close to the inlet, because the IC carrier flow exhibits very low background conductivity. Without the electrophoretic current, the CE could not be operated. Therefore, in order to maintain a continuous carrier flow through the IC transfer capillary without resulting in a breakdown of the electrophoretic current in the electrolyte vessel, the modulator used for the IC×CE coupling of the present invention is adapted, to manage sequential injections of segments of the IC carrier flow from the outlet of the IC transfer capillary into the inlet of the CE capillary. In other words, it is essential that volume segments instead of a continuous flow are injected into the CE capillary. This is achieved by injector means providing for discrete volume parts of effluent being injected.

The modulator can be any injector device that provides for delivering discrete volume segments of effluent from the IC system to the CE system. In the following, two preferred embodiments for a modulator/injector are described in more detail, i.e. a guidance and positioning system and a valve system. In a first alternative, the distance between the outlet of the transfer capillary and the inlet of the CE capillary is modified periodically, also defined as cycling, preferably by a microprocessor-controlled guidance and positioning system, which governs the movement of the outlet of the transfer capillary towards and away from the inlet of the separation capillary and/or the movement of inlet of the separation capillary towards and away from the outlet of the transfer capillary. In its initial position, the distance between outlet of the transfer capillary and inlet of the separation capillary is too large for hydrodynamic transfer of the liquid zone emerging from the outlet of the transfer capillary to occur. In this condition IC effluent enters the electrolyte solution without entering the CE separation capillary. The movement of the outlet of the transfer capillary towards the inlet of the separation capillary, or the movement of the inlet of the separation capillary towards the outlet of the transfer capillary, or the movement of both, reduces the distance until defined hydrodynamic transfer between the capillaries can occur. This transfer is called injection. At least one of the capillaries is guided and positioned from a first position to a second position to change the distance between outlet of the transfer capillary and inlet of the separation capillary such that in a first position, when both, outlet and inlet, are in a distance from each other, an injection does not occur, and in a second position, when both, outlet and inlet, are close to each other, an injection occurs. Both capillaries can be arranged in axial direction, sideways or in any other direction that allows for guidance and positioning, preferably until they are in alignment. Preferably, the capillaries are moved in axial direction. Either the separation capillary or the transfer capillary can be in a fixed position. Alternatively, both capillaries can be moved towards and away from the other capillary. Preferably, the CE separation capillary is in a fixed position and the transfer capillary is moved in axial direction.

It has been found that a further advantage of the injection by movement of the capillary/capillaries is obtained, i.e. that by the movement, a convection in the electrophoresis buffer in the electrolyte vessel is caused, which dilutes the emerging IC carrier flow, and thereby minimizes the influence of the IC carrier flow on the stability of the electrophoretic current. This allows using this system without the need for stirring, such as a mechanical stirrer in the electrolyte vessel. Therefore, although a stirrer can be used for a device of the present invention, it is not necessary and in one embodiment the CE system does not comprise a stirrer.

In another embodiment, convection in the electrophoresis buffer in the electrolyte vessel can be caused by a stirrer, which can be operated continuously, or intermittently, e.g. only during the interval between injection steps. The use of a stirrer can be useful to reduce the distance between the outlet of the transfer capillary and the inlet of the separation capillary during the interval in between injection steps, as the emerging IC carrier flow is rapidly diluted by the convection caused by the stirring. As in the method of the present invention operation of a stirrer is not essential because the movement of the capillary/capillaries is causing sufficient convection for operation of the CE, but can be still useful for some embodiments, the skilled artisan can choose the optimal conditions, either with or without a separate stirrer.

In a second alternative, a switching valve is used between the outlet of the transfer capillary and the IC system. The valve can be positioned near the outlet of the IC column, or near the outlet of the transfer capillary. The opening and shutting of the valve can be controlled by a microprocessor and is timed to inject segments of IC carrier flow into the separation capillary. The part of the carrier flow that is not used for CE separation can either be discarded or can flow into the electrolyte vessel. In this case the distance between the outlet of the transfer capillary and the inlet of the separation capillary can be smaller and kept constant, because between injection steps, no IC carrier flow is emerging and affecting the integrity of the electrophoretic circuit.

The volume of the segments to be injected can be determined in accordance with the conditions used, such as the CE system, the sample composition etc. The skilled artisan can find the optimal volume in routine experiments. Preferred ranges are described below.

Other means for cycling or dosing volume segments, i.e. providing discrete volume segments intermittently can be used.

The device of the present invention can additionally comprise detection means for analysis of the IC and/or CE effluent. Detectors for IC and CE systems are known in the art and can be used for the present device accordingly. Preferably, a mass spectrometer is used. Thus, in a preferred embodiment the outlet of the CE capillary can be connected with a mass spectrometer for the detection of the substance zones separated by IC×CE.

DEFINITIONS

Figure 1:
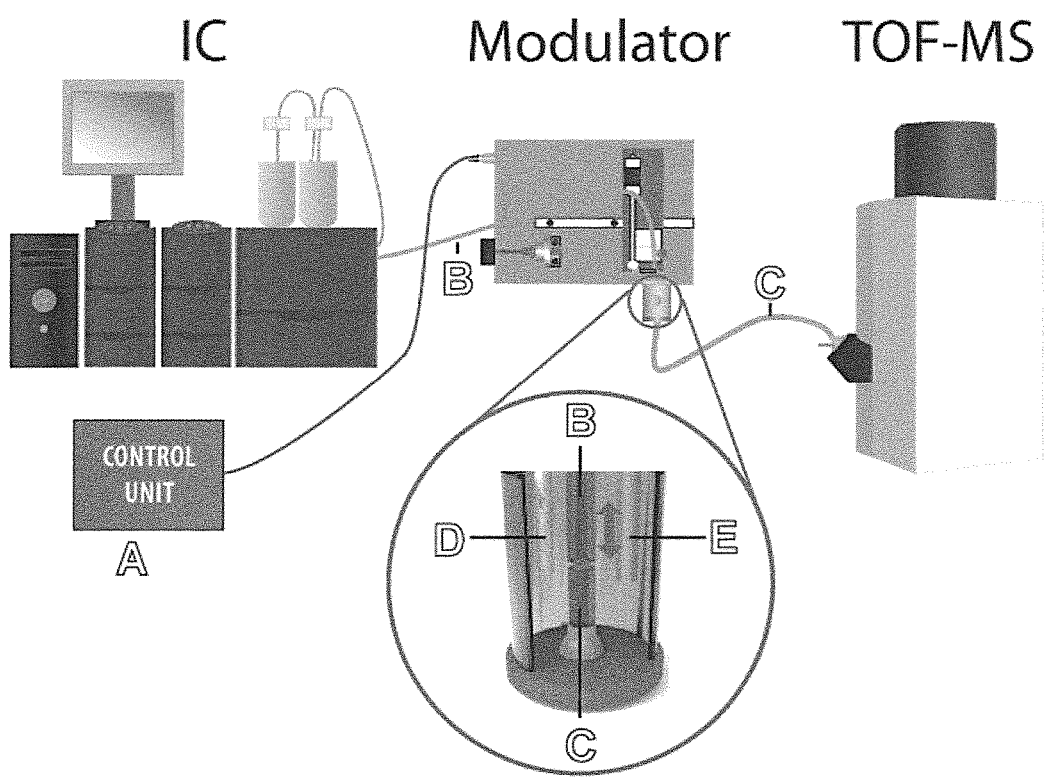
FIG. 1 shows the basic structure of a two-dimensional separation system of the present invention for on-line coupling of ion chromatography (IC) and capillary electrophoresis (CE) in conjunction with mass spectrometric (MS) detection.
(A): microprocessor-based controller of the IC×CE coupling with sequential upward and downward movement of the IC transfer capillary (B), and switching function (On/Off) of the stirrer (E); (B): IC transfer capillary; (C): CE separation capillary; (D): platinum high voltage electrode for the CE separation; (E): stirrer; IC system: ICS-5000 (Thermo); MS system: micrOTOF-MS (Bruker Daltonics)

Ion chromatography (most commonly ion-exchange chromatography) is a process that allows the separation of ions and charged polar molecules based on their affinity to the ion exchanger. It can be used for almost any kind of charged species or molecule that can form ionic species, any molecule that can be protonated or deprotonated. Examples of suitable substances include inorganic compounds, like salts, acids and bases, or organic molecules, like large proteins, small nucleotides and amino acids. Typically, the sample is loaded onto the column in the form of an aqueous solution and an eluent, i.e. an aqueous solution with suitable eluting power, known as the mobile phase, is used to carry the sample through the column comprising the stationary phase. The stationary phase is typically a resin or gel matrix consisting of agarose or cellulose beads with covalently bonded charged functional groups. The target analytes (anions or cations) are retained on the stationary phase but can be eluted by increasing the concentration of a similarly charged species that will displace the analyte ions from the stationary phase. For example, in anion exchange chromatography, the negatively charged analyte could be displaced by a rather high hydroxide ion concentration in the mobile phase. The analytes of interest can be detected by detector means, typically by using their conductivity or UV/Visible light absorbance for detection.

Capillary electrophoresis (CE) is an analytical technique that separates ions based on their electrophoretic mobility with the use of an applied high voltage. The electrophoretic mobility is dependent upon the charge of the ion and the hydrodynamic radius. The rate at which the ion moves is directly proportional to the applied electric field—the greater the field strength, the faster the speed of migration. Neutral species have no specific mobility but are transported by the so-called electro-osmotic flow. If two ions are the same size, the one with greater charge will exhibit higher electrophoretic mobility. For ions of the same charge, the smaller ion has less friction and overall higher electrophoretic mobility. Capillary electrophoresis is attractive because it provides high separation efficiency.

"Suppression" or "suppressor" is used for IC to increase analyte signal in case of conductivity detection. The background conductivity of the chemicals used to elute analyte species from the ion-exchange column is reduced. This improves the conductivity measurement of the ions being tested. When using IC with suppression the IC carrier flow or effluent has low background conductivity, corresponding to pure or ultrapure water. The use of suppressors in IC is well-known and the skilled person can find suitable ones easily. An optimal suppressor is one that provides an effluent with a background conductivity as low as possible.

The term "continuous" when used in the present description refers to a continuous operation in contrast to a batch-wise operation. In particular it refers to a method where the IC carrier flow or effluent is continuously transferred from the IC system through the transfer capillary to the injector, where it is injected on-line, without interrupting the operation of the IC or CE system, into the CE capillary. This does not exclude that the flow can encompass short interruptions, e.g. by shutting off a valve in the modulator between the IC system and the CE system.

"On-line coupling" means that the two separation methods are coupled in a way that allows continuous separation and detection of the ionic species via both separation techniques in sequence.

"Injection" means the transfer of a discrete volume segment of the IC carrier flow or effluent from the outlet of the transfer capillary to the inlet of the separation capillary and the entrance into the separation capillary. One interval of injection is comprising the injection time $t_{inj}$, the preinjection time $t_{preinj}$, and the time the positioning unit of the modulator needs to move the capillary from injection position to preinjection position and backwards (see also FIG. 3).

"Nanoliter volume" means volumes of less than 1 µl.

"Volume segments" are discrete volumes of the effluent that are created by injector means, for example by modifying the distance between transfer and separation capillary or by a valve.

"Ionic species" means ions or molecules that can be charged. Examples are substances that dissociate or can be protonated or deprotonated in solution, such as organic molecules like amino acids, peptides and proteins, nucleotides, or inorganic compounds like acids, bases, salts etc.

"Time increment" means a predetermined time period, in particular a time period that is used in the cycling mode.

"Effluent" or "IC carrier flow" is used interchangeably and defines the mobile phase that flows out of the IC column or capillary, respectively.

"Sample" is a composition that shall be analyzed and usually is an aqueous solution of analytes.

"Analyte" can be any substance that can be analyzed with an IC×CE system, such as anions and cations.

The term "cycling" refers to a mode of injection that is preferably used in the method of the present invention, where repeatedly volume segments are provided and injected intermittently.

DETAILED DESCRIPTION OF THE INVENTION

The present invention provides devices and a method for two-dimensional IC×CE separation of ionic species, wherein the two separation methods are coupled on-line, and with continuous operation.

The device comprises an ion chromatography (IC) system, which comprises a suppressor. By using a suppressor, the effluent obtained from the IC column comprises a solution having low background conductivity with the analyte species separated therein. This causes a so-called "stacking" effect during the sequential injection into the CE system, due to the differences in conductivity of the electrophoresis buffer and injected sample solution, which result in a sharpening of the injected bands and in a signal amplification. IC systems are known and the known systems can be used for the device and the method of the present invention.

With an IC×CE system of the present invention, wherein the analyte zones separated by IC are present in a carrier flow of solution having low background conductivity after suppression, it is possible to apply a short injection interval of less than 10 s, preferably of less than 2 s, in order to keep effects on the electrophoretic current low and to apply narrow injection segments. Preferably the IC system is a capillary IC system.

The IC carrier flow is transferred via a transfer capillary either partially or completely, into an electrolyte vessel comprising an electrophoresis buffer, and a high voltage electrode, preferably a platinum electrode. CE systems with short separation capillaries (<50 cm) can be used. In a typical CE system an electric field is maintained permanently during the operation of the IC×CE via the electrode and the electrophoresis buffer. This voltage is about 1-100 kV; preferably it is about 10 to 35, more preferably 15 to 30 kV. The field is maintained between the electrode and the grounded interface. Usually the outlet of the electrophoresis buffer filled CE separation capillary is connected with a detector, preferably a mass spectrometer.

The electrolyte vessel comprises an electrophoresis buffer, which has a volume which is significantly higher than the volume of the volume segments emerging from the outlet of the transfer capillary between injection steps. For example, the volume segments being in the nanoliter range, the volume of the electrophoresis buffer can be in the range of 1 to 10 ml, such as about 2 ml. In this way, it is ensured that the influence of the IC carrier flow on the stability of the electrophoretic current is ensured. This influence can be further minimized by causing a convection in the buffer, for example by movement of the capillary and/or by the operation of a stirrer. The optimal conditions can be selected by the skilled person depending on the size of the electrolyte vessel and the selected flow rate of the IC carrier flow. The CE buffer should be replaced in the electrolyte vessel at appropriate intervals to ensure stable electrophoretic separations as it is known to the skilled person. It has been found that an IC carrier flow rate less than 10 µl/min is preferable as it leads to good results. With higher flow rates the effect of the IC carrier flow on the integrity of the electrophoretic circuit could be compromising for the stability of the CE. A flow rate in the range of 1 to 8, such as about 5 µl/min is preferred (see also Example 3). Higher flow rates until up to 10 µl/min can be applied. Potential detrimental effects on the stability of the electrophoretic current can then be compensated by causing convection in the electrophoresis buffer to rapidly dilute the IC carrier flow. This can for example be achieved by a switchable stirrer, which is optionally switched on during the interval between injection steps, or by other known devices creating convection.

To avoid any interference, the transfer capillary connecting the IC system with the electrolyte vessel should be made of nonconductive material, such as fused silica or plastic; preferably it is made of fused silica. The separation capillary is also preferably made of fused silica. The fused silica capillaries can be coated with polyimide. The polyimide coating can then be removed at the ends of the capillary prior to use. For example, the polyimide coating can be removed at the end of the capillary at a length of about 5 mm. Furthermore, prior to use, both ends of the separation capillary and the injection end of the transfer capillary can be polished with polishing papers, preferably with a grit size of 32 µm and 12 µm, preferably at an angle of about 90°, to smoothen the surface. Furthermore, prior to use, the separation capillary can be flushed to condition the capillary. For example the separation capillary can be flushed sequentially with 100 mM NaOH, preferably for about 10 minutes, with ultrapure water from a Milli-Q system, preferably for about 10 minutes, and with the background electrolyte, preferably for about 30 minutes. The background electrolyte can consist of a 25 mM ammonium acetate buffer adjusted with ammonia to pH=9.15. The buffers used in the application are preferably filtered prior to use, for example by a syringe filter (0.2 µm). Moreover, the size of the transfer capillary should be adapted to the volume to be used and to the size of IC column and CE capillary. Preferably, the transfer capillary has an inner diameter of less than 500 µm; preferably the inner diameter is in the range of 150 to 50 µm, such as about 75 µm.

The essential part of the device of the present invention is a modulator, which controls the transfer of IC carrier flow from the IC transfer capillary into the CE system. The modulator comprises a transfer capillary and injector means.

Injector means, optionally regulated or controlled by a microprocessor, provide for the creation of volume segments that are injected in time increments rather than continuously. Any device that can provide for intermittent delivery of volume segments of the effluent from the transfer capillary can be used. In preferred embodiments either a positioning and guidance system for modifying the distance between transfer capillary and separation capillary or a valve system are used. In one embodiment the injection, the time increments and the volume segments, respectively, are controlled by adjusting the distance between the outlet of the transfer capillary and inlet of the separation capillary regularly, or by opening and shutting a switching valve in the transfer capillary. Distance adjustment can be achieved by movement of one or both of the capillaries towards and away from the other capillary. This movement is controlled by a positioning and guidance system, optionally controlled by a microprocessor. Transfer of IC carrier flow into the CE system can occur, when the distance between the openings of the capillaries is small enough to allow transfer of a defined volume segment of IC carrier flow by hydrodynamic force.

In a preferred embodiment, the modulator comprises a microprocessor, which, in the first alternative, controls the movement of the transfer capillary towards and away from the inlet of the CE separation capillary. Every few seconds small volume segments are sequentially injected into the inlet of the separation capillary by the microprocessor-controlled movement of the IC transfer capillary, for example in axial direction (see B in FIG. 1). The movement starts from an initial or first position of the transfer capillary, wherein the distance between outlet of the transfer capillary and inlet of the separation capillary is selected so that the liquid zone emerging from the outlet of the transfer capillary does not enter the inlet of the CE capillary hydrodynamically. This distance is reduced to a smaller distance between the outlet of the transfer capillary and the inlet of the separation capillary, or even until direct contact is achieved, i.e. to the second position. At this smaller distance, a defined hydrodynamic transfer of the liquid zone into the inlet of the CE capillary can occur. Suitable distances depend on the overall hydrodynamic situation in the electrolyte vessel, which depend e.g. on the flow rate through the transfer capillary, the amount of stirring and/or convection in the electrolyte vessel, or the flow velocity in the CE system. The flow rate should be selected such that between injection steps, excessive IC carrier flow into the electrophoresis buffer is avoided. In this way, less IC carrier flow comprising the analyte is lost, and the electrophoretic current is less affected.

In a preferred embodiment, the modulator is a modified capillary batch injection (CBI) device. Briefly, the modulator consists of a vertical positioning unit moving the transfer capillary, which is fixed on a holder, up and down in axial direction (see arrow in detailed part of FIG. 1 showing the electrolyte vessel). This can be achieved by a 1.8° stepper motor with leadscrew which reaches a positioning precision of 1 µm/step. The end of the transfer capillary can be guided through a 0.38 mm inner diameter glass guide (Hilgenberg, Malsfeld, Germany), fixed in a purpose-built manual x,y-positioner, into the electrophoretic vessel. With help of the positioning unit the transfer capillary is aligned with the separation capillary, which is located in axial direction on the bottom of the electrophoretic vessel. Positioning can be controlled using a laboratory-modified microscopic video camera (e.g. DigiMicro 1.3, dnt, Dietzenbach, Germany). The electrophoretic vessel cell can be further equipped with a stirrer. The rate of injection steps or the timely sequence of volume segments depends on the separation speed of the CE system. All components of the first volume segment injected into the CE separation capillary preferably have already reached the detector, before the next volume segment is injected. In this way it is ensured that all signals detected can be unambiguously assigned to the respective volume segment injected into the CE. Basically, it is ensured that ionic species of a subsequent injected volume segment cannot overtake ionic species of the previously injected volume segment in the CE separation capillary. The interval in between injection steps depends, inter alia, on the length of the CE separation capillary used. The shorter the column, the shorter the interval in between injections steps can be. In an example that is described later, the CE separation capillary was 20.5 cm in length, which allowed an interval of about 17 seconds. This interval comprises the injection time $t_{inj}$ of 2 s and the pre-injection time $t_{preinj}$ of 15 seconds. In the case of co-electroosmotically migrating species shorter preinjection intervals of less than 10 s can be possible.

The exact distances between the outlet of the transfer capillary and the inlet of the separation capillary must be adapted to the experimental conditions, which can be done by the skilled person. A typical flow rate for a capillary IC system is less than 10 µl/min, preferably about 1 to about 8, such as about 5 µl/min. With a higher flow rate, there is a risk that the volume of IC carrier flow is not injected into the CE separation capillary, leading to a dilution of the electrophoresis buffer. This could affect the stability of the electrophoretic current necessary for the operation of the CE. In one embodiment a cycling between a distance of less than 100 µm for injection, and more than 150 µm in the intermittent period, is used. In other words, during injection mode a typical distance between outlet of the transfer capillary and the inlet of the separation capillary is less than 100 µm. The distance between the injection cycles is typically increased to greater than about 150 µm. If a stirrer is used, the suitable distances can be reduced. For example, the distance during injection mode can be from about 30 to about 50 µm.

The injection time, governed by either the length of time in which the capillaries are positioned in injection mode (short distance), or by the time in which the switching valve is open, can be up to 10 seconds. Preferably, the injection time is about 2 seconds.

After injection, the transfer capillary or the separation capillary, or both, is/are moved back to the initial position. The rapid homogeneous distribution of liquid, which has emerged from the outlet of the transfer capillary, in the electrolyte vessel but has not been injected into the separation capillary, can be supported by switching on a stirrer (see E in FIG. 1). However, the use of a stirrer is optional. The results shown in FIG. 2 were obtained without stirring. In addition to the mass spectrometric detection, which generates the detection signals for the IC×CE separation, also the conductivity detection of the IC can be recorded and can be used in addition for the analytical evaluation.

In another preferred embodiment, the capillaries are both in a fixed position, and the modulator is associated with a switching valve which controls the IC carrier flow through the transfer capillary by opening and shutting the valve. The switching valve can be positioned near or at the inlet of the transfer capillary, or near or at the outlet of the transfer capillary, or anywhere in between. In other words, the valve can withdraw small volumes of effluent directly at the outlet of the IC column and deliver those volume segments via the transfer capillary to the CE capillary, where the outlet of the transfer capillary is in a position to allow injection into the CE capillary. In another embodiment, the effluent of the IC column is transferred completely or partially to the transfer capillary and the valve being positioned near or at the outlet of the transfer capillary provides for the delivery of suitable volume segments to the inlet of the CE capillary. The switching valve can be opened and shut in a controlled manner, optionally controlled by a microprocessor, leading to injection intervals corresponding to the injection intervals achieved by the sequential movement described for the first alternative of the modulator above. During the time period, wherein the switching valve is open, defined liquid segments are transferred hydrodynamically from the outlet of the transfer capillary to the inlet of the CE separation capillary. One advantage of this alternative solution is that only in the injection interval carrier liquid is introduced into the CE system. This embodiment is particularly useful for those IC systems where a high carrier flow is obtained.

The devices of the present invention further comprise a capillary electrophoresis (CE) separation capillary. To obtain optimal results, the separation capillary should be as short as possible. It has been found, that a separation capillary having a length of less than 50 cm can be used, preferably the capillary has an inner diameter of less than 100 µm. Preferably, the separation capillary is less than 35 cm, more preferably less than 25 cm in length, and has an inner diameter in the range of about 35 to about 20, such as about 25 µm. The inlet of the separation capillary, in one embodiment, is essentially in axial alignment with the outlet of the transfer capillary.

Preferably, the devices of the present invention further comprise an interface connecting the outlet of the separation capillary with a detector. For example, the short CE separation capillary, which is filled with electrophoresis buffer, can be coupled at its outlet to a commercial "sheath flow"—electrospray ionization (ESI) interface for combination with a mass spectrometer. In the electrolyte vessel, a high voltage between the electrophoresis buffer and the ESI interface ground can be maintained permanently via a platinum electrode placed in the electrolyte vessel (see D in FIG. 1).

The device of the present invention can be used in a method of the present invention for two-dimensional separation of ionic species by on-line coupling of ion chromatography and capillary electrophoresis (IC×CE), comprising the sequential injection of volume segments of the IC carrier flow into the CE system The method of the present invention for two-dimensional separation of ionic species by online coupling of ion chromatography (IC) and capillary electrophoresis (CE), comprises the following steps:

a) injecting a sample into an IC system comprising a suppressor;

b) transferring IC effluent through a transfer capillary to a CE system comprising an electrolyte vessel with electrophoresis buffer, a separation capillary and a high voltage electrode;

c) injecting volume segments of effluent into a separation capillary of the CE system via injector means.

In a first step, a sample is loaded onto an IC system. This IC system is preferably a capillary IC system. The sample can be any compound or mixture of compounds, which comprises ions under operating conditions. For example, the sample can comprise mixtures of amino acids, or nucleotides, or cyclic nucleotides or any other substance that can form ionic species as a result of dissociation or protonation/deprotonation as defined above. In a second step, the ionic species in the sample are separated in the IC system and suppressed. After suppressing the ions, the analyte is present in solution, usually aqueous solution with low background conductivity, for example in highly pure water. The solution containing the analyte zones is the IC carrier flow or effluent, which is then transferred via and through a transfer capillary as defined above to the outlet of the transfer capillary, which ends in the electrophoresis buffer comprised in an electrolyte vessel as defined above.

In a third step, volume segments of IC carrier flow or effluent are injected into the inlet of the separation capillary via injection means, as defined above.

If the sample containing ionic species to be separated comprises a mixture of amino acids, the separation conditions are preferably selected so that the amino acids are present in the sample as anionic species during separation by IC. This can be achieved by using an alkaline IC buffer. The separation conditions should then be selected so that the amino acids separated by IC and injected into the separation capillary are present as cationic species during separation by CE. This can be achieved by using an acidic CE buffer such as formiate. A formiate buffer is also compatible with the subsequent detection technique such as mass spectrometry. By switching from anionic species to cationic species between the two combined separation techniques by selecting alkaline and acidic buffers, the efficiency of the combined separation techniques is increased due to the difference in selectivity caused by the different states of charge. Furthermore, the injection frequency can be increased because CE separation can be achieved more rapidly with cationic analytes compared to anionic analytes.

In one alternative, the transfer is controlled by movement of one or both of the capillaries towards and away from each other, for example in their axial direction. As soon as the distance between the openings of both capillaries is small enough to allow hydrodynamic transfer of a defined volume of IC carrier flow, injection occurs. For example, if the separation capillary is in a fixed position, and the modulator comprised a positioning and guidance system for the movement of the transfer capillary, the transfer capillary is then moved to set a distance of less than 100 µm between the outlet of the transfer capillary and the inlet of a separation capillary of a CE system. This short distance is then kept for less than 10 seconds. During this time period, which is also termed injection period, a defined volume segment is introduced/injected into the inlet of the separation capillary of the CE system. After the injection step the transfer capillary is moved to increase the distance between the outlet of the transfer capillary and the inlet of the separation capillary of the CE system to about more than 150 µm. During these steps, the IC carrier flow is continuous.

The CE carrier flow can then be transferred to a detector via an interface as described above. For example, the separation capillary, which is filled with electrophoresis buffer, can be coupled at its outlet to a commercial "sheath flow"—electrospray ionization (ESI) interface for coupling to a mass spectrometer. The injection steps can be repeated until the IC carrier flow is processed to the latest zone eluting from the IC.

During the method usually a high voltage of about 1-100 kV, preferably of about 20 kV, is maintained between the electrode in the electrolyte vessel and the interface between the separation capillary outlet and the detector.

FIG. 2 illustrates the result of an IC×CE separation with mass spectrometric detection of a mixture of nucleotides and cyclic nucleotides. The graph shows the intensities of the extracted mass spectrometric signals according to the retention time of the IC and the migration time of the CE. With this relatively simple model mixture of six components, the significant increase in the peak capacity by the realized IC×CE separation is illustrated. While using IC some nearly co-eluting bands with base peak widths of 1-1.5 min can not be separated in the first dimension, the CE in several cases allows a separation with high separation efficiency (base peak widths of a few seconds). In FIG. 2 it can be seen that the substances cCMP, CMP, AMP and cAMP are only partially or not at all separated in the first separation dimension (IC). The IC×CE, however, leads to a complete separation of all model compounds and allows a significant increase in peak capacity due to the high separation efficiency of CE and due to the orthogonality of IC and CE. This shows the superiority of the online coupled IC×CE method of the present invention.

EXAMPLES

Example 1

A sample comprising nucleotides and cyclic nucleotides was subjected to a two-dimensional separation using ion chromatography (IC) and capillary electrophoresis (CE). The IC comprised a suppressor to provide effluent comprising the analytes in highly pure water.

The sample was injected into the IC system and continuously eluted. The IC effluent was transferred through a non-conductive transfer fused silica capillary to an electrolyte vessel of a CE system containing electrophoresis buffer. Nanoliter volume segments of the effluent were injected into the separation capillary of the CE system by continuously modifying the distance between transfer capillary and separation capillary. The distance between the outlet of the transfer capillary and the inlet of the separation capillary, which were in axial alignment, for injecting a nanoliter volume segment was moved such that the outlet of the transfer capillary had a distance of 50 µm to the inlet of the separation capillary. The short distance was kept for 2 seconds such that a volume segment could enter the inlet of the separation capillary of the CE system and then the transfer capillary was withdrawn in axial direction to increase the distance to 300 µm. This distance was maintained for 15 seconds, before the next injection was done. The movement of the transfer capillary was controlled by a modulator comprising a positioning and guidance system controlled by a microprocessor. A high voltage of about 20 to 25 kV was maintained between the electrode in the electrolyte vessel and the interface between the separation capillary outlet and the detector.

For IC the following separation conditions were used: IonSwift MAX-200 anion column; eluent: 40 mM KOH; injection volume: 0.4 µl; flow rate; 5 µL/min; transfer capillary: 60 cm in length/75 µm inner diameter (ID)

For the CE separation the following conditions were used: electrophoresis buffer: 25 mM $NH_4Ac/NH_3$ pH 9.15; capillary dimensions: 20.5 cm in length/25 µm inner diameter; separation voltage: 22.5 kV; injection time: 2 seconds each; interval between two consecutive injections: 17 seconds.

Figure 2A:
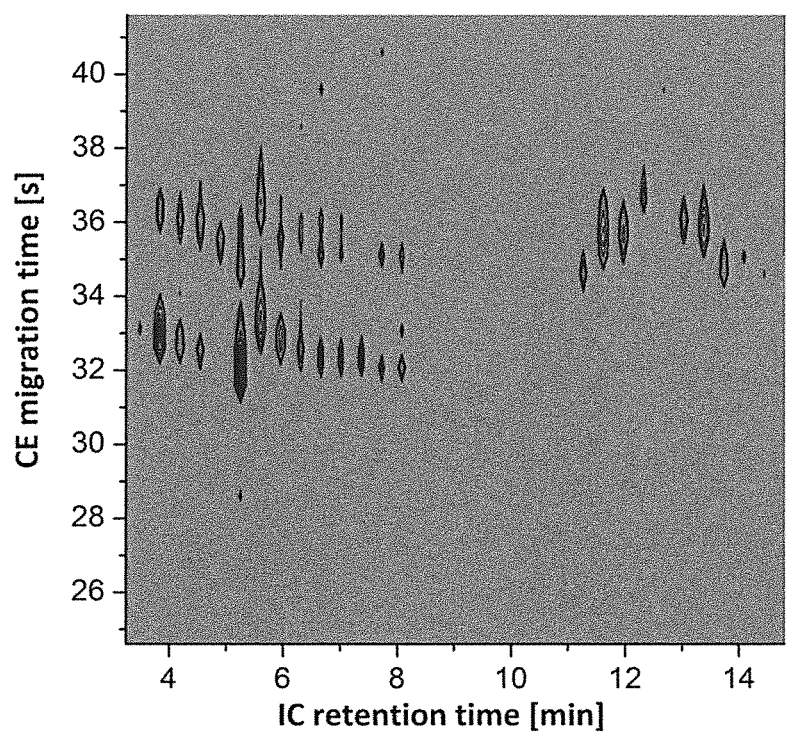
FIG. 2 shows the result of a two-dimensional separation IC×CE of nucleotides and cyclic nucleotides as a contour plot (a) and as a combined chromatoelectropherogram (b); substances: AMP, GMP, CMP (each 300 µM), and cAMP, cGMP, cCMP (each 100 µM); separation conditions IC: IonSwift MAX-200 anion column; eluent: 40 mM KOH; injection volume: 0.4 µl; flow rate; 5 µL/min; transfer capillary: 60 cm in length/75 µm inner diameter (ID); CE separation conditions: separation buffer: 25 mM $NH_4Ac$/ $NH_3$ pH 9.15; capillary dimensions: 20.5 cm in length/25 µm inner diameter; separation voltage: 22.5 kV; injection time: 2 seconds each; interval between two consecutive injections: 17 seconds.
Figure 2B:
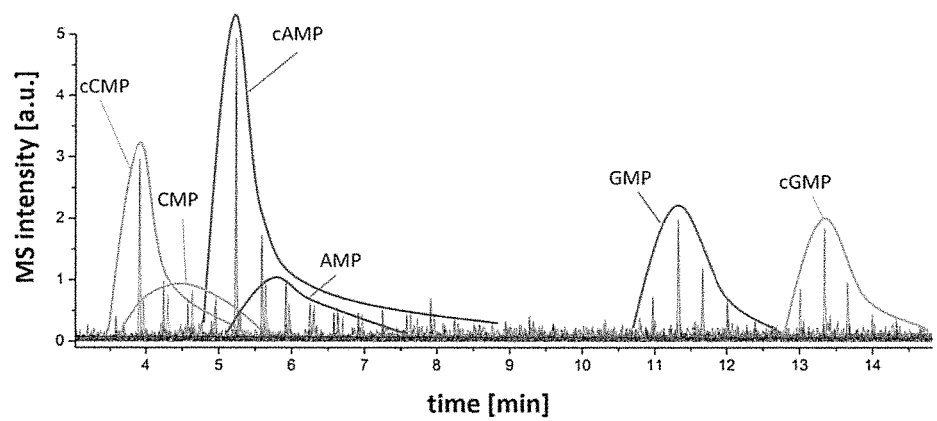

The results are shown in FIGS. 2a and 2b.

FIG. 2a shows the result of the two-dimensional separation IC×CE of nucleotides and cyclic nucleotides as a contour plot.

FIG. 2b shows in a combined chromatoelectropherogram that nucleotides and cyclic nucleotides could be resolved by using the method of the present invention. As can be seen the peaks for AMP, GMP, CMP (each 300 µM), and cAMP, cGMP, cCMP (each 100 µM) are clearly separated.

Example 2

A further sample comprising nucleotides and cyclic nucleotides was subjected to a two-dimensional separation using ion chromatography (IC) and capillary electrophoresis (CE) as described above in Example 1 with the following additional details.

Prior to using fused silica capillaries (Polymicro Technologies, Phoenix, Ariz., USA) in the separation techniques the capillaries were prepared and conditioned as follows. Both ends of the separation capillary (length=20.5 cm, inner diameter=25 µm) and the injection end of the transfer capillary (length=60 cm, inner diameter=75 µm) were polished with polishing papers (32 µm and 12 µm grit size) at a 90° angle until the surface was smooth. The polyimide coating was removed at a length of about 5 mm. Before each use, the separation capillary was flushed 10 minutes with 100 mM NaOH, 10 minutes with ultrapure water from a Milli-Q system, and 30 minutes with the background electrolyte consisting of a 25 mM ammonium acetate buffer adjusted with ammonia to pH=9.15. The buffer was filtrated before use with a syringe filter (0.2 µm) (Carl-Roth, Karlsruhe, Germany). The measurements were performed applying a separation voltage of 22.5 kV.

An ICS-5000 (Dionex, Thermo Scientific) ion chromatograph was used for capillary-scale IC separations. It consisted of a dual pump module with both capillary (pump 1) and analytical pump (pump 2), an eluent generator module (EG KOH 300 with subsequent trap column), and a detector/chromatography module. The latter module comprises an in-line eluent degasser, a four-port injection valve (injection volume, 0.4 µL), a column oven, an anion capillary eluent suppressor, and a conductivity detector.

The capillary high performance (cHPIC) detector/chromatography module was thermally controlled at 10° C. Dionex Ion-Swift MAX-200 column (0.25×250 mm) with appropriate guard column (0.25×50 mm), both operated at 35° C., were used for anionic separation.

Instrument control and data acquisition were performed using Chromeleon 6.8 software. The eluent concentration (KOH) was kept constant at 40 mM hydroxide during a run.

A modified capillary batch injection (CBI) device was used as modulator to control the transfer of the IC effluent by a movable transfer capillary (FIG. 1B) into the CE separation capillary. The modulator consists of a vertical positioning unit moving the transfer capillary, which is fixed on a holder, up and down in axial (z) direction (see arrow in detailed part of FIG. 1 showing the electrolyte vessel). This is achieved by a 1.8° stepper motor with leadscrew which reaches a positioning precision of 1 µm/step. The end of the transfer capillary is guided through a 0.38 mm inner diameter glass guide (Hilgenberg, Malsfeld, Germany), fixed in a purpose-built manual x,y-positioner, into the electrophoretic vessel. With help of the positioning units the transfer capillary is aligned with the separation capillary, which is located in axial direction on the bottom of the electrophoretic vessel. Positioning is controlled using a laboratory-modified microscopic video camera (DigiMicro 1.3, dnt, Dietzenbach, Germany).

A micrOTOF-MS (Bruker Daltonik, Massachusetts, USA) with a coaxial sheath liquid electrospray interface (Agilent Technologies, California, USA) was used for detection. A mixture of 2-propanol, water, and ammonia (49.9:49.9:0.2, v/v/v) was used as sheath liquid at a flow rate of 8 µl/min. Nebulizer gas pressure was set to 1 bar. The electrospray voltage was 4 kV.

Example 3

Figure 3:
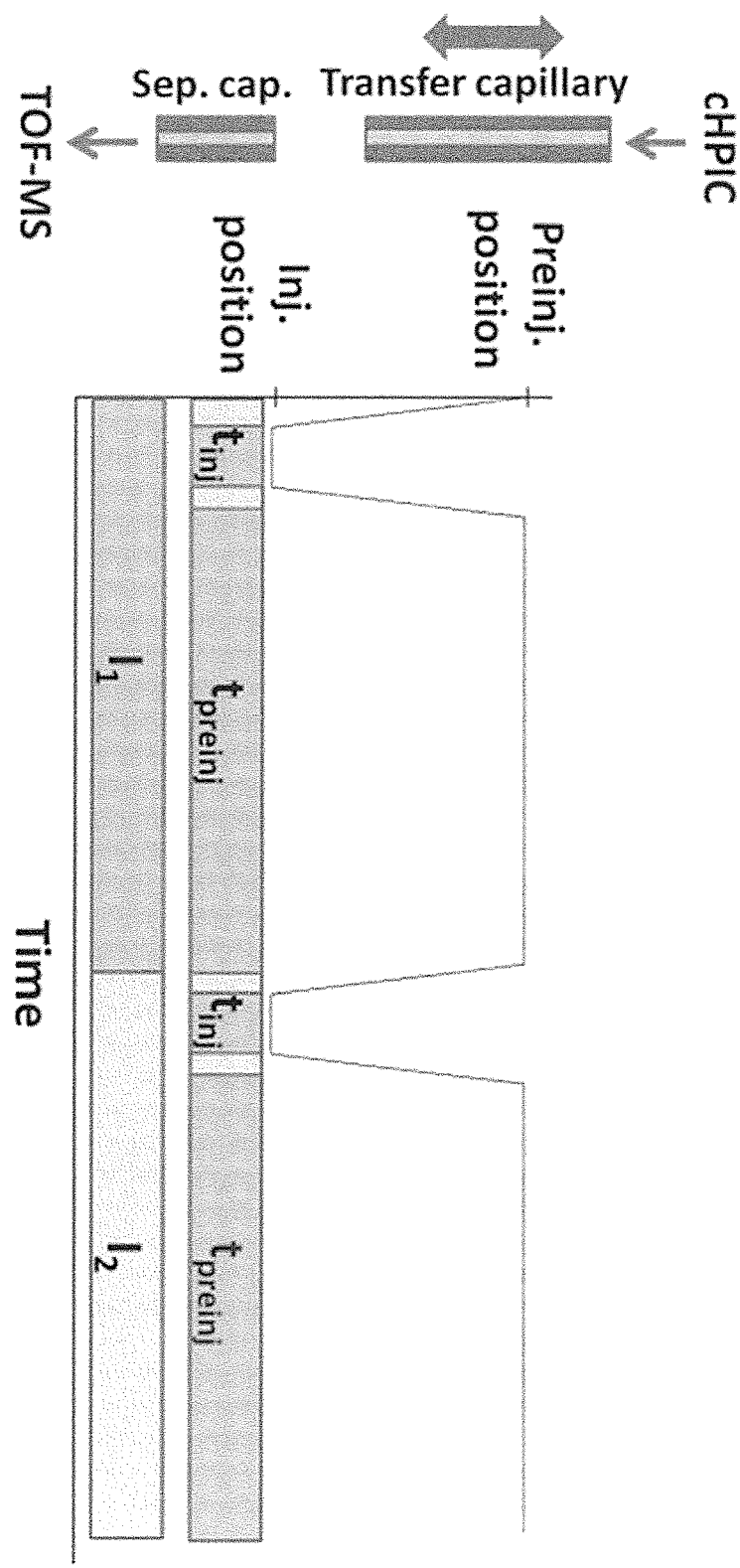
FIG. 3 shows an illustration of the modulation process (movement of the transfer capillary towards the separation capillary). One injection interval (I) comprises injection time $t_{inj}$, pre-injection time $t_{preinj}$ and the time the stepper motor needs to switch between them.

Modulation times of the IC×CE-MS measurements of a model system comprising a mixture of nucleotides (AMP, GMP, CMP) and cyclic nucleotides (cAMP, cGMP, cCMP) were studied and optimized as illustrated in FIG. 3. These experiments were performed without IC. Instead, a syringe pump (UMP3, WPI, Florida, USA), a microliter syringe (1000 µl Nanofil syringe, WPI), and a fused silica injection capillary (inner diameter=75 µm) were used. The injection capillary was axially aligned with the separation capillary and moved periodically up and down from injection to preinjection positions while the sample was expelled continuously with a flow rate of 5 µl/min. The syringe was filled with a model solution containing 150 µM AMP and 50 µM cAMP in pure water. The CE high voltage source was permanently set to 22.5 kV. To optimize the injection times, measurements were performed with injection times of 1, 2, 4, and 8 seconds whereas the preinjection time was kept at 15 seconds. Furthermore, the preinjection time was varied (60, 30, 20, 15, 10, 6, and 2 seconds) using an injection time of 2 seconds in order to optimize the preinjection time. The shortest preinjection time possible without overloading the capillary was 15 seconds. A further reduction of preinjection times resulted in double peaks and separation was no longer accomplished. 2 seconds were chosen as smallest injection interval possible for this model system being a compromise between small injection intervals and still sufficient signal intensities.

Example 4

The IC flow rate was optimized by performing IC×CE–MS measurements (AMP, GMP, CMP, 300 µM each; cAMP, cGMP, cCMP, 100 µM each) at different flow rates (2, 5, and 8 µl/min). Low flow rates led to peak broadening. Higher flow rates resulted in a better IC separation efficiency. However, the flow rate is one of the determining factors for the amount of substance injected into the CE capillary. The IC effluent mainly consisted of pure water. Thus, the higher the flow rate the more water was injected into the capillary. Each injection led to a reduction of electrophoretic current, which was recovering during the preinjection time. The drop of current increased with higher flow rates. The electrophoretic current dropped significantly (to 1-2 µA) or broke down completely with flow rates higher than 8 µl/min. This rendered any effort for separation impossible. Thus, 5 µl/min were chosen for all following measurements. At this flow rate current fluctuations were in an acceptable range with an electrophoretic current of 5.5-7 µA.

Example 5

Furthermore, the effect of sample stacking in cHPIC×CE–MS measurements was investigated. Sample stacking in the CE separation capillary occurs when the specific conductivity of the back-ground electrolyte is higher than the specific conductivity of the sample plug. In the IC×CE–MS setup the IC effluent, which was injected into the CE, consisted of analyte zones in pure water due to the suppressor. The effect of stacking during IC×CE–MS measurements was examined by means of a setup comparable to IC×CE–MS where the IC was replaced by a microsyringe pump. Mixtures of cAMP and AMP (50 µM cAMP, 150 µM AMP) dissolved in water or in background electrolyte were used as samples. The respective sample was filled into the syringe and the flow rate of the pump was set to 5 µl/min. For the measurements the high voltage source was permanently set to 22.5 kV. The optimized modulation times as described in Example 3 were used. Before the first injection the capillary was kept 10 seconds in preinjection position to equilibrate the flow of the pump. Then, 5 intervals of injection were performed and the electropherograms were compared. The separation efficiency and peak heights of analytes were significantly enhanced in case of the sample dissolved in water compared to the sample prepared in background electrolyte as a result of the stacking effect.

REFERENCES

[1] Jandera, P; "Comprehensive two-dimensional liquid chromatography—practical impacts of theoretical considerations. A review" (Central European Journal of Chemistry 10 (2012), pp. 844-875

[2] J. Scott Mellors et al; "Hybrid Capillary/Microfluidic System for Comprehensive Online Liquid Chromatography-Capillary Electrophoresis-Electrospray Ionization-Mass Spectrometry"; Anal. Chem., 2013, 85 (8), pp. 4100-4106

[3] Brudin, S. S. et al.: "Comprehensive two-dimensional liquid chromatography: ion chromatography x reversed-phase liquid chromatography for separation of low-molar-mass organic acids." J. Chromatography A, 1217, 2010, pp. 6742-6746.

[4] Niegel, C. et al.: "Fast separations by capillary electrophoresis hyphenated to electrospray ionization time-of-flight mass spectrometry as a tool for arsenic speciation analysis." Analyst, 2012, 137, pp. 1956-1962.

[5] Matysik, F. M. et al.: "Verfahren und Vorrichtung zur Untersuchung von Proben im Nanoliter-Bereich mittels Kapillar-Batch-Injektions-Analyse." DE 197 17 738 C1 (1997).

[6] Matysik, F. M.: "Capillary batch injection—a new approach for sample introduction into short-length capillary electrophoresis with electrochemical detection." Electrochemistry Comm. 8, 2006, pp. 1011-1015.

The invention claimed is:

1. Device for continuous two-dimensional separation of ionic species comprising
   a) an ion chromatography (IC) system, comprising a suppressor;
   b) a capillary electrophoresis (CE) system comprising an electrolyte vessel, a high voltage electrode, and a CE separation capillary; and
   c) a modulator, for transferring effluent of the IC system to the CE system, comprising a transfer capillary and injector means, wherein the injector means are adapted to provide discrete volume segments of effluent, wherein the injector means comprises a positioning and guidance system for modifying the distance between the outlet of the transfer capillary and the inlet of the CE separation capillary in a controlled manner, wherein the CE separation capillary or the transfer capillary or both are configured for movement in an axial direction.

2. The device of claim 1, wherein the injector means comprises a switching valve between the transfer capillary and the CE separation capillary for controlling and guiding volume segments of the effluent to the inlet of the separation capillary.

3. The device of claim 1, wherein the injector means comprises a microprocessor for controlling the provision and/or delivery of volume segments.

4. The device of claim 1, wherein the CE separation capillary is a short capillary electrophoresis (CE) separation capillary, which is less than 50 cm in length, and has an inner diameter of less than 100 µm, wherein the inlet of the separation capillary is in alignment with the outlet of the transfer capillary.

5. The device according to claim 1, further comprising a detector connected to the outlet of the separation capillary, wherein optionally the detector is a mass spectrometer.

6. Method for two-dimensional separation of ionic species by online coupling of ion chromatography (IC) and capillary electrophoresis (CE), comprising the following steps:
   a) injecting a sample into an IC system comprising a suppressor;

b) transferring IC effluent through a transfer capillary to a CE system comprising an electrolyte vessel with electrophoresis buffer, a separation capillary and a high voltage electrode; and c) after step b) injecting volume segments of effluent to a separation capillary of the CE system via injector means, wherein the distance between the outlet of the transfer capillary and the inlet of the separation capillary of the CE system is periodically modified between a first position and a second position by movement of one or both capillaries, wherein the first position provides for a distance of more than 150 µm and the second position provides for a distance of less than 100 µm, wherein the movement is controlled by a modulator comprising a positioning and guidance system, wherein the movement of the CE separation capillary or the transfer capillary or both is in an axial direction.

7. The method of claim 6, wherein the second position providing for a distance of less than 100 µm is kept for less than 10 seconds, wherein during this step a volume segment is introduced into the inlet of the separation capillary of the CE system.

8. The method of claim 6, wherein the IC system is a capillary system, and wherein the flow rate in the capillary IC system is less than 10 µl/min.

9. The method of claim 6, wherein conductivity of the IC carrier flow is detected.

10. The method of claim 6, wherein a detector is connected to the outlet of the separation capillary, wherein optionally the detector is a mass spectrometer, coupled via a sheath flow electrospray ionization (ESI) interface.

11. Method of claim 6, wherein a distance of less than 100 µm between the outlet of the transfer capillary and the inlet of the CE separation capillary is kept for less than 2 seconds, and/or wherein a distance between the outlet of the transfer capillary and the inlet of the separation capillary of the CE system is between 10 and 50 µm; and/or wherein a distance between the outlet of the transfer capillary and the inlet of the CE separation capillary of the CE system is from about 200 to 350 µm.

12. Method of claim 6, wherein the separation capillary is in a fixed position, and the movement of the transfer capillary is controlled by the positioning and guidance system.

* * * * *